United States Patent [19]

Seifert et al.

[11] Patent Number: 4,900,827
[45] Date of Patent: Feb. 13, 1990

[54] PROCESS FOR THE PREPARATION OF PYRIMIDINE DERIVATIVES

[75] Inventors: Gottfried Seifert, Magden; Robert Hässig, Gipf-Oberfrick, both of Switzerland

[73] Assignee: Ciba-Geigy Corporation, Ardsley, N.Y.

[21] Appl. No.: 288,751

[22] Filed: Dec. 22, 1988

[51] Int. Cl.$^4$ .......................................... C07D 239/52
[52] U.S. Cl. ..................................................... 544/303
[58] Field of Search ........................................ 544/303

[56] References Cited

U.S. PATENT DOCUMENTS

| | | | |
|---|---|---|---|
| 4,500,344 | 2/1985 | Freerksen | 71/93 |
| 4,542,216 | 9/1985 | Pfluger | 544/320 |
| 4,545,811 | 10/1985 | Meyer et al. | 91/93 |
| 4,692,524 | 9/1987 | Hässig | 544/303 |

FOREIGN PATENT DOCUMENTS

| | | |
|---|---|---|
| 0072347 | 2/1983 | European Pat. Off. . |
| 0084020 | 7/1983 | European Pat. Off. . |
| 0094790 | 11/1983 | European Pat. Off. . |

OTHER PUBLICATIONS

Meyer et al., CA 98-215616q (1983).
Freerksen et al., CA 101-7181x (1984).

*Primary Examiner*—Mukund J. Shah
*Assistant Examiner*—Cecilia Shen
*Attorney, Agent, or Firm*—Edward McC. Roberts

[57] ABSTRACT

4,6-Bis(difluoromethoxy)pyrimidines of formula I

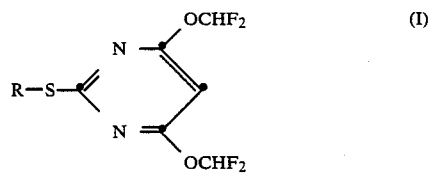

wherein R is $C_1$-$C_4$alkyl or unsubstituted or substituted phenyl or benzyl, are prepared by reacting a 4,6-dihydroxypyrimidine dialkali metal salt of formula II

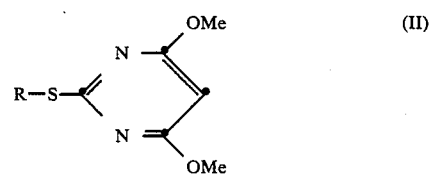

wherein R is as defined for formula I and Me is an alkali metal, with chlorodifluoromethane in a solvent selected from the group consisting of ketones and alkyl cyanides, in the presence of 0.05 to 1.1 mol of water per mol of dialkali metal salt of formula II.

21 Claims, No Drawings

PROCESS FOR THE PREPARATION OF PYRIMIDINE DERIVATIVES

The present invention relates to a process for the preparation of 4,6-bis(difluoromethoxy)pyrimidines of formula I

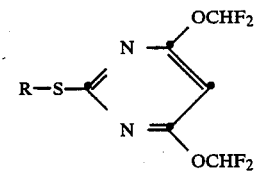

wherein R is $C_1$-$C_4$alkyl or unsubstituted or substituted phenyl or benzyl.

By alkyl is meant straight chain or branched alkyl, for example methyl, ethyl, n-propyl, isopropyl, n-butyl or the butyl isomers.

Suitable substituents of phenyl or benzyl are, for example, alkyl, halogen, nitro or alkoxy.

The 4,6-bis(difluoromethoxy)pyrimidines of formula I are valuable intermediates. They can be converted, for example by oxidation, into the corresponding sulfones which, when further reacted with ammonia or a primary amine, yield the corresponding 2-amino-4,6-bis(difluoromethoxy)pyrimidines which, in turn, when further reacted with a suitable phenylsulfonyl isocyanate or N-(phenylsulfonyl)carbamate, yield herbicidally active sulfonylureas. Such herbicidally active sulfonylureas are disclosed, for example, in published European patent applications A-0 072 347, A-0 084 020 and A-0 094 790.

It is known to prepare 4,6-bis(difluoromethoxy)-pyrimidine by reacting 4,6-dihydroxypyrimidine with chlorodifluoromethane in dioxane in the presence of aqueous soldium hydroxide. This process affords 4,6-bis(difluoromethoxy)-2-methylthiopyrimidine in a yield of only 25% of theory (q.v. U.S. Pat. No. 4,542,216, Example 5). In contrast, the conversion into the 2-methylsulfonyl-4,6-bis(difluoromethoxy)pyrimidine and the reaction thereof to 2-amino-4,6-bis(difluoromethoxy)pyrimidine give very good to quantitative yields.

It is therefore the object of the present invention to provide a process for the preparation of 4,6-bis(difluoromethoxy)pyrimidines of formula I in which these compounds can be prepared in good yield.

Accordingly, the present postulates preparing the 4,6-bis(difluoromethoxy)pyrimidines of formula I by reacting a 4,6-dihydroxypyrimidine dialkali metal salt of formula II

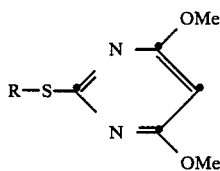

wherein R is as defined for formula I and Me is an alkali metal, with chlorodifluoromethane in a solvent selected from the group consisting of ketones and alkyl cyanides, in the presence of 0.05 to 1.1 mol of water per mol of dialkali metal salt of formula II.

Suitable solvents selected from the group of the ketones are, for example, acetone, methyl ethyl ketone, diethyl ketone, methyl isopropyl ketone or methyl isobutyl ketone. Suitable alkali metal cyanide solvents are, for example, acetonitrile or propionitrile. Preferred solvents are acetonitrile, propionitrile, acetone and methyl ethyl ketone. A particularly preferred solvent is acetonitrile. The above mentioned solvents are conveniently used in an amount of 500 to 1000 ml per mol of dialkali metal salt of formula II.

Starting materials and final products of the process of this invention are known. The dialkali metal salts of formula II can be prepared in a manner known per se from the corresponding 4,6-dihydroxypyrimidines, for example by reaction with alkali metal hydroxides or alkali metal alcoholates.

The reaction of the dialkali metal salt of formula II with chlorodifluoromethane can be carried out with particular advantage in the presence of 0.13 to 0.6 mol of water per mol of dialkali metal salt of formula II.

The process of the invention can be carried out in a wide temperature range. Particularly suitable reaction temperatures are in the range from $+20°$ to $+100°$ C. It is preferred to carry out the reaction in the temperature range from $+40°$ to $+60°$ C.

The reaction of the dialkali metal salt of formula II with chlorodifluoromethane can also be conveniently carried out in the presence of a phase transfer catalyst. The phase transfer catalyst can be used in an amount of 0.01 to 0.25 mol per mol of dialkali metal salt of formula II. It is preferred to use 0.05 to 0.15 mol of phase transfer catalyst per mol of dialkali metal salt of formula II.

Suitable phase transfer catalysts are typically quaternary ammonium salts and crown ethers. Preferred phase transfer catalysts are 18-crown-6, benzyltrimethylammonium chloride, tetrabutylammonium chloride, tetramethylammonium methyl sulfate and tetramethylammonium chloride. Tetramethylammonium chloride is especially preferred.

The reaction of the dialkali metal salt of formula II with chlorodifluoromethane can be carried out under normal pressure or under elevated pressure. The reaction is preferably carried out under elevated pressure. Suitable pressures are in the range from 1 to 100 bar. A preferred pressure range in which the reaction may be carried out is from 1 to 20 bar.

An equimolar amount or an excess of chlorodifluoromethane may be used.

It is convenient to use an amount of 2 to 10 mol of chlorodifluoromethane per mol of dialkali metal salt of formula II. An amount of 4 to 6 mol of chlorodifluoromethane per mol of dialkali metal salt of formula II is preferred.

A preferred embodiment of the process of this invention comprises reacting a disodium salt of formula II with chlorodifluoromethane in the presence of 0.13 to 0.6 mol of water and 0.05 to 0.15 mol of tetramethylammonium chloride per mol of disodium salt of formula II, in 500 to 1000 ml of acetonitrile per mol of disodium salt of formula II, in the temperature range from $+40°$ to $+60°$ C. and under a pressure of 1 to 20 bar.

The process of this invention makes it possible to prepare the 4,6-bis(difluoromethoxy)pyrimidines of formula I, starting from the 4,6-dihydroxypyrimidine alkali metal salts of formula II, in yields of up to 68% of theory, whereas, as mentioned at the outset, a yield of only 25% of theory is obtainable by the known prior art process.

A further advantage of the process of the invention is that the chlorodifluoromethane, which is used in excess, can be reused for a fresh batch, whereas in the known processes it is lost through hydrolysis.

The following Examples illustrate the process of the invention in more detail.

EXAMPLE 1:

Peparation of 4,6-bis(difluoromethoxy)-2-methylthiopyrimidine

In a stirred autoclave, 101 g of anhydrous 4,6-dihydroxy-2-methylthiopyrimidine disodium salt and 8 g of trimethylammonium chloride are mixed with 500 ml of acetonitrile and 2.5 g of water. After closing the autoclave and heating to +50° C., 215 g of chlorodifluoromethane are added over 15 minutes from a steel feed vessel, whereupon the pressure in the autoclave rises to 2 bar.

After a reaction time of 4 hours the autoclave is ventilated. The reaction mixture is then filtered and the filter residue is washed with acetonitrile. The solvent is removed by distillation under vacuum at +80° C. and the product melt is washed with 200 ml of hot water, affording 98 g (68% of theory) of 4,6-bis(difluoromethoxy)-2-methylthiopyrimidine in 90% purity.

EXAMPLE 2:

The procedure of Example 1 is repeated, using acetone instead of acetonitrile, to give 78 g of 4,6-bis(difluoromethoxy)-2-methylthiopyrimidine (54% of theory) in 90% purity.

EXAMPLE 3:

The procedure of Example 1 is repeated, replacing 4,6-dihydroxy-2-methylthiopyrimidine disodium salt by the corresponding 4,6-dihydroxy-2-methylthiopyrimidine dipotassium salt, to give 54 g (38% of theory) of 4,6-bis(difluoromethoxy)-2-methylthiopyrimidine in 90% purity.

EXAMPLE 4:

The procedure of Example 1 is repeated, replacing tetramethylammonium chloride by benzyltrimethylammonium chloride, tetrabutylammonium chloride or tetramethylammonium methyl sulfate, to give the same yield of product as in Example 1.

What is claimed is:

1. A process for the preparation of a 4,6-bis(difluoromethoxy)pyrimidine of formula I

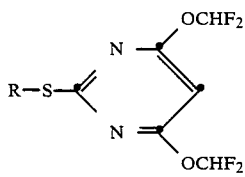

wherein R is $C_1$-$C_4$alkyl, phenyl or benzyl, which process comprises reacting a 4,6-dihydroxypyrimidine dialkali metal salt of formula II

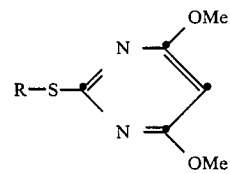

wherein R is as defined for formula I and Me is an alkali metal, with chlorodifluoromethane in a solvent selected from the group consisting of ketones and alkyl cyanides, in the presence of 0.05 to 1.1 mol of water per mol of dialkali metal salt of formula II.

2. A process according to claim 1, wherein the solvent is selected from the group consisting of acetone, methyl ethyl ketone, diethyl ketone, methyl isopropyl ketone, methyl isobutyl ketone, acetonitrile and propionitrile.

3. A process according to claim 1, wherein the reaction of the dialkali metal salt of formula II with chlorodifluoromethane is carried out in the presence of 0.13 to 0.6 mol of water per mol of dialkali metal salt of formula II.

4. A process according to claim 1, wherein the solvent is selected from the group consisting of acetonitrile, acetone and methyl ethyl ketone.

5. A process according to claim 1, wherein the solvent is acetonitrile.

6. A process according to claim 1, wherein 500 to 1000 ml per mol of solvent is used per mol of compound of formula II.

7. A process according to claim 1, wherein Me is sodium or potassium.

8. A process according to claim 1, wherein the reaction of the dialkali metal salt of formula II with chlorodifluoromethane is carried out in the presence of a phase transfer catalyst.

9. A process according to claim 8, wherein the phase transfer catalyst is a quaternary ammonium salt or a crown ether.

10. A process according to claim 8, wherein the phase transfer catalyst is selected from the group consisting of 18-crown-6, benzyltrimethylammonium chloride, tetrabutylammonium chloride, tetramethylammonium methyl sulfate and tetramethylammonium chloride.

11. A process according to claim 8, wherein 0.01 to 0.25 mol of phase transfer catalyst is used per mol of dialkali metal salt of formula II.

12. A process according to claim 8, wherein 0.05 to 0.15 mol of phase transfer is used per mol of dialkali metal salt of formula II.

13. A process according to claim 8, wherein the phase transfer catalyst is tetramethylammonium chloride.

14. A process according to claim 1, wherein the dialkali metal salt of formula II is reacted with chlorodifluoromethane in the temperature range from +20° to +100° C.

15. A process according to claim 1, wherein the dialkali metal salt of formula II is reacted with chlorodifluoromethane in the temperature range from +40° to +60° C.

16. A process according to claim 1, wherein the dialkali metal salt of formula II is reacted with chlorodifluoromethane under a pressure of 1 to 100 bar.

17. A process according to claim 1, wherein the dialkali metal salt of formula II is reacted with chlorodifluoromethane under a pressure of 1 to 20 bar.

18. A process according to claim 1, wherein Me is sodium.

19. A process according to claim 1, wherein 2 to 10 mol of chlorodifluoromethane is used per mol of dialkali metal salt of formula II.

20. A process according to claim 1, wherein 4 to 6 mol of chlorodifluoromethane is used per mol of dialkali metal salt of formula II.

21. A process according to claim 1, which comprises reacting a disodium salt of formula II with chlorodifluoromethane in the presence of 0.13 to 0.6 mol of water and 0.05 to 0.15 mol of tetramethylammonium chloride per mol of disodium salt of formula II, in 500 to 1000 ml of acetonitrile per mol of disodium salt of formula II, in the temperature range from $+40°$ to $+60°$ C. and under a pressure of 1 to 20 bar.

* * * * *